US008454983B2

(12) United States Patent
DeChant et al.

(10) Patent No.: US 8,454,983 B2
(45) Date of Patent: *Jun. 4, 2013

(54) FORMULATION AND DELIVERY OF BACILLUS THURINGIENSIS SUBSPECIES ISRAELENSIS AND BACILLUS SPHAERICUS IN COMBINATION FOR BROADSPECTRUM ACTIVITY AND MANAGEMENT OF RESISTANCE TO BIOLOGICAL MOSQUITO LARVICIDES

(75) Inventors: Peter DeChant, Portland, OR (US); Bala N. Devisetty, Buffalo Grove, IL (US)

(73) Assignee: Valent BioSciences Corporation, Libertyville ( * ) Notice: Subject to any disclaimer, the term of this patent is extended or adjusted under 35 U.S.C. 154(b) by 35 days.

This patent is subject to a terminal disclaimer.

(21) Appl. No.: 13/115,623

(22) Filed: May 25, 2011

(65) Prior Publication Data

US 2011/0229543 A1    Sep. 22, 2011

Related U.S. Application Data

(63) Continuation of application No. 11/112,362, filed on Apr. 22, 2005, now Pat. No. 7,989,180, which is a continuation-in-part of application No. 10/074,782, filed on Feb. 13, 2002, now abandoned.

(60) Provisional application No. 60/269,513, filed on Feb. 16, 2001.

(51) Int. Cl.
| | |
|---|---|
| *A01N 25/26* | (2006.01) |
| *A01N 25/24* | (2006.01) |
| *A01N 63/00* | (2006.01) |
| *C12N 1/20* | (2006.01) |
| *C12P 1/04* | (2006.01) |
| *A01N 25/22* | (2006.01) |
| *A01N 25/30* | (2006.01) |
| *A01N 27/00* | (2006.01) |
| *C12N 3/00* | (2006.01) |

(52) U.S. Cl.
USPC ..... 424/405; 424/84; 424/93.46; 424/93.461; 435/41; 435/170; 435/242; 435/252.1; 435/252.31

(58) Field of Classification Search
USPC ................. 424/84, 93.461, 405; 435/41, 170, 435/242, 252.1, 252.31
See application file for complete search history.

(56) References Cited

U.S. PATENT DOCUMENTS

| | | | |
|---|---|---|---|
| 4,166,112 A | 8/1979 | Goldberg | |
| 4,818,534 A | 4/1989 | Levy | |
| 4,865,842 A | 9/1989 | Bradbury et al. | |
| 4,985,251 A | 1/1991 | Levy | |
| 5,273,749 A | 12/1993 | Bok et al. | |
| 5,275,815 A | 1/1994 | Payne | |
| 5,501,852 A | 3/1996 | Meadows et al. | |
| 5,518,897 A | 5/1996 | Stevens, Jr. et al. | |
| 5,560,909 A | 10/1996 | Rheaume et al. | |
| 5,847,079 A | 12/1998 | Payne | |
| 5,912,162 A | 6/1999 | Liu et al. | |
| 6,077,521 A | 6/2000 | Hammond et al. | |

FOREIGN PATENT DOCUMENTS

| | | |
|---|---|---|
| DE | 4133889 A1 | 4/1993 |
| WO | WO 96/28973 | 9/1996 |
| WO | WO 98/28984 A | 7/1998 |
| WO | WO 98/39973 | 9/1998 |
| WO | WO 02/48069 A | 6/2002 |

OTHER PUBLICATIONS

Chabanenko, A.A., et al., Efficiency of Combined Preparation from *Bacillus sphaericus* and *Bac. Thuringiensis* H-14 Against Bloodsucking Mosquito Larvae, Group of Arthors, 1992, UDK 615-285. 036, Moscow.

Wirth, Margaret C., et al., Cyt1A from *Bacillus thuringiensis* Synergizes Activity of *Bacillus sphaericus* against *Aedes aegypti* (Diptera: Culicidae), Applied and Environmental Microbiology, Mar. 2000, pp. 1093-1097; vol. 66, No. 3, California.

Tianyong, Li, et al., Coexpression of cyt1 Aa of *Bacillus thuringiensis* subsp. *Israelensis* with *Bacillus sphaericus* Binary Toxin Gene in Acrystalliferous Strain of *B. thuringiensis*; Current Microbiology, 1000, pp. 322-326; col. 40; New York.

Wirth, Margaret C., et al., Cyt1A from *Bacillus thuringiensis* Restores Toxicity of *Bacillus sphaericus* Against Resistant *Culex quinquefasciatus* (Diptera: Culicidae); J. Med. Entomol., 2000; pp. 401-407 vol. 37(3); California.

Porter, A.G., Mosquitocidal Toxins, Genes and Bacteria: The Hit Squad; Parasitology Today, 1996; p. 175-180; vol. 12. No. 5, Republic of Singapore.

Wirth, Margaret C., et al., Cyt1Ab1 and Cyt2Ba1 from *Bacillus thuringiensis* subsp. Medellin and *B. thuringiensis* subsp. *Israelensis* Synergize *Bacillus sphaericus* against *Aedes aegypti* and Resistant *Culex quinquefasciatus* (Diptera: Culcidae); Applied and Environmental Microbiology; Jul. 2001; pp. 3280-3284; vol. 67, No. 7, France.

(Continued)

*Primary Examiner* — Jon P Weber
*Assistant Examiner* — Kailash C Srivastava
(74) *Attorney, Agent, or Firm* — Wood, Phillips, Katz, Clark & Mortimer

(57) ABSTRACT

A method for controlling Dipteran larvae or a method for inhibiting the development of larvicidal resistance, controlling resistant populations and reducing resistance levels in Diptera by introducing a larvicidally-effective amount of a combination of a strain of *Bacillus thuringiensis* subspecies *israelensis* and a strain of *Bacillus sphaericus* into an environment containing Dipteran larvae; and a composition of the combination are disclosed. Preferably both strains are non-genetically modified.

28 Claims, No Drawings

OTHER PUBLICATIONS

Rao, D.R., et al., Development of a High Level of Resistance to *Bacillus sphaericus* in a Field Population of *Culex quinquefasciatrus* from Kochi India, Journal of the America Mosquito Association, 1995, 1191):1-15; India.

Nielsen-Leroux, Christina, et al., Resistance to *Bacillus sphaericus* Involves Different Mechanisms in *Culex pipiens* (Diptera: Culcidae) Larvae; J. Med. Entomol.; 1997; pp. 321-327, vol. 34(3); France.

Charles, C-F., et al., *Bacillus sphaericus* Toxins: Molecular Biology and Mode of Action; Annual Review of Entomology, 1996, pp. 451-472; vol. 41, California.

Bar, E., et al., Cloning and Expression of *Bacillus thuringiensis israelensis* δ-Endotoxin DNA in *B. sphaericus*; Journal of Invertibrate Pathology, pp. 149-158, vol. 57, Israel.

Yuan, Zhiming, et al., High-Level Field Resistance to *Bacillus sphaericus* C3-4I in *Culex quinquefasciatus* from Southern China, Biocontrol Science and Technology, 2000, pp. 41-49; vol. 10, China.

Davidson, Elizabeth W., et al., Comparative Field Trials of *Bacillus sphaericus* Strain 1593 and *B. thuringiensis* var. *israelensis* Commericial Powder Formulations; J. Econ. Entomol., 1981, pp. 350-354; vol. 74, America.

Trisrisook, Mayuree, et al., Molecular Closing of the 130-Kilodalton Mosquitocidal δ-Endotoxin Gene of *Bacillus thuringiensis* subsp. *Israelensis* in *Bacillus sphaericus*, Applied and Environmental Microbiology, Jun. 1996; pp. 1710-1716; vol. 56, No. 6;Thisland.

Poopathi, S., et al., Evaluation of Synergistic Interaction Between *Bacillus spohaericus* and *Bacillus thuriengiensis* Var. *Israelensis* Against *Culex quiquefasciatus* Resistant and Susceptical to *B. sphaericus* 1593M; J. Ecobio 1999; pp. 289-298; vol. 11(4) India.

Lee, H. L., et al., Preliminary Field Evaluation of Indigenous (Malaysian) isolates and Commerical Preparation of *Bacillus thuringiensis* Serotype H-14 and *Bacillus sphaericus* serotype H5a5B against *Anopheles* Karwari; Tropical Biomedicine; 1990; pp. 49-57, vol. 7; India.

Federici, Brian A., et al., Cyt1Aa Protein of *Bacillus thuringiensis* is Toxic to the Cottonwood Leaf Beetle, *Chrysomela scripta*, and Suppresses High Levels of Reisistance to Cry3Aa; Applied and Environmental Microbiology; Nov. 1998, pp. 4368-4371; vol. 64, No. 11; America.

Wirth, M.C., et al., CytA enables CryIV Endotoxins of *Bacillus thuringiensis* to overcome high levels of CryIV resistance in the mosquito, *Culex quiquefasciatus*; Proc. Natl. Acad. Sci. USA, Sep. 1997; pp. 10536-10540; vol. 94; California.

Bar, E., et al., Expression of Chromosomally Inserted *Bacillus thuringiensis Israelensis* Toxin Genes in *Bacillus sphacricus*, Journal of Invertebrate Pathology, 1998; pp. 206-213; vol. 72; Kenya.

Bar, E., et al., The Introduction into *Bacillus sphaericus* of the *Bacillus thuriensis* subsp. Medellin cyt1Ab1 Gene Results in Higher Susceptibility of Resistant Mosquito Larva Populations to *B. sphaericus*, Applied and Environmental Microbiology; Oct. 1998; pp. 3910-3916; vol. 64, No. 10, Columbia.

Silva-Filha, Maria-Helena, et al., Low-Level Resistance to *Bacillus sphaericus* in a Field-Treated Population of *Culex quinquefasciatus* (Diptera; Culcidae); J. Econ. Entomol. 1995; pp 525-530; vol. 88(3); America.

Mulla, Mir S., et al., Emergene of Resistance and Resistance Management in Field Populations of Tropical *Culex quinquefasciatus* to the Microbia Crontrol Agent *Bacillus sphaericus*; Journal of the American Mosquito Control Association; 2003; pp. 39-46, vol. 19(1), India.

Rodcharoen et al., "Journal of Economic Entomology", vol. 87, No. 5, 1994, pp. 1133-1140.

Wirth et al., "Journal of Medical Entomology", vol. 37, No. 3, 2000, pp. 401-407.

Krainova et al.."Biological larvicide used to control mosquitos is based on *Bacillus thuringiensis israilensis* and additional *Bacillus sphaericus* preparates", Abstr of RU2111667 patent, May 27, 1998.

Poncet S. et al. Improvement of *Bacillus Sphaericus* toxicity against Dipteran larvae by integration, via homologous recombination of the CRY11A toxin gene from *Bacillus thuringiensis* subsp. *Israelensis*. Applied and Environmental Microbiology, Washington, D.C., US, vol. 63, No. 11, Nov. 1997, pp. 4413-4420.

Sun, F. et al. Reduction of resistance of *Culex pipiens* larvae to the binary toxin from *Bacillus sphaericus* by coexpression of Cry4Ba from *Bacillus thuringiensis* subsp. *Israelensis* with the binary toxin gene. Retrieved from STN Database accession No. 135:328357 and World Journal of Microbiology & Biotechnology (2001), 17(4), 385-389.

Sun, F. et al. Synergism reaction between mosquitat larvicidal gene products from *Bacillus sphaericus* and *B. thuringiensis* subsp, *Israelensis*. Retrieved from STN Database accession No. 136:97797—abstract Zhongguo Bingduxue (2000), 15 (Suppl.), 116-119. (Abstract only from EPO), Full publication can be accessed by Chemical Abstracts Service, Attn.: Document Detective Service, 2540 Olentangy River Road, Columbus, OH 43202, U.S.A.

International Search Report (Dated Nov. 27, 2002); Written Opinion (Dated Feb. 24, 2004) and Supplementary European Search Report (Dated Jan. 27, 2004).

Servant, et al., Production of Cry11A and Cry11Ba Toxins in *Bacillus sphaericus* Confers Toxicity towards *Aedes aegypti* and Resistant *Culex* Populations, Applied and Environmental Microbiology, Jul. 1999, p. 3021-3016, Thivernal-Grignon, France.

Eldridge, Bruce F., et al., Bacterial Mosquito Larvicides: Present Status of Knowledge and Future Directions for Research, Proceedings and Papers of the 56th Annual Conference of the California Mosquito and Vector Control Association, 1988, p. 117-127, University of California, Davis and Riverside.

Wirth, Margaret C., et al., Laboratory Selection for Resistance to *Bacillus sphaericus* in *Culex quinquefasciatus* (Diptera: Culicidae) from California, USA, J. Med. Entomol. 37(4): 534-540 (2000).

FORMULATION AND DELIVERY OF BACILLUS THURINGIENSIS SUBSPECIES ISRAELENSIS AND BACILLUS SPHAERICUS IN COMBINATION FOR BROADSPECTRUM ACTIVITY AND MANAGEMENT OF RESISTANCE TO BIOLOGICAL MOSQUITO LARVICIDES

CROSS-REFERENCE TO RELATED APPLICATION

This application is a Continuation of U.S. application Ser. No. 11/112,362 filed Apr. 22, 2005 which is a Continuation In Part of U.S. application Ser. No. 10/074,782, filed Feb. 13, 2002 which claims priority of U.S. 60/269,513 filed on Feb. 16, 2001.

FIELD OF THE INVENTION

The invention is directed to a method for controlling Dipteran larvae or a method for inhibiting larvicidal resistance in Diptera by introducing a larvicidally-effective amount of a novel combination of a strain of *Bacillus thuringiensis* subspecies *israelensis* and a strain of *Bacillus sphaericus* into an environment containing Dipteran larvae; and a composition of the combination. Preferably, both strains are non-genetically modified.

BACKGROUND OF THE INVENTION

Mosquitoes and black flies are representative of the order Diptera which are pests that have plagued humans and animals for generations. Mosquitoes are the major vectors for a number of human and animal diseases, including malaria, yellow fever, viral encephalitis, dengue fever and filariasis.

Various chemical pesticides have been developed with the goal of controlling Diptera. For example, treatment of a water source with a water-soluble alcohol in water-miscible form for mosquito abatement is disclosed in U.S. Pat. No. 6,077,521. However, more recent emphasis has been placed on the use of biopesticides. For example, controlled-release formulations of at least one biological pesticidal ingredient are disclosed in U.S. Pat. No. 4,865,842; control of mosquito larvae with a spore-forming *Bacillus* ONR-60A is disclosed in U.S. Pat. No. 4,166,112; novel *Bacillus thuringiensis* isolates with activity against Dipteran insect pests are disclosed in U.S. Pat. Nos. 5,275,815 and 5,847,079; a biologically pure culture of a *Bacillus thuringiensis* strain with activity against insect pests of the order Diptera is disclosed in U.S. Pat. No. 5,912,162 and a recombinantly derived biopesticide active against Diptera including cyanobacteria transformed with a plasmid containing a *B. thuringiensis* subsp. *israelensis* dipteracidal protein translationally fused to a strong, highly active native cyanobacteria's regulatory gene sequence is disclosed in U.S. Pat. No. 5,518,897.

Yet even these biopesticides have drawbacks; so the search for new biopesticides continues. One drawback of certain biopesticides is the potential build-up of pesticidal resistance.

Resistance is defined by differences in susceptibility that arise among populations of the same species exposed to a pesticide continuously over a period of time. These differences are identified by observing a statistical shift in the lethal dose (LD) either to kill 50% or 95% of the population ($LD_{50}$ or $LD_{95}$ respectively). Individual differences in susceptibility exist within each species, and pests that are substantially less susceptible may be present, generally at low frequencies, in at least some of the wild populations. In the presence of the pesticide, it is these substantially less susceptible pests that survive and reproduce. Since their ability to survive is a result of their genetic makeup, their resistant genetic makeup is then passed on to their offspring, resulting in shifts in the populations' susceptibility via pesticide-induced selection. Resistance to larvicides has been encountered among certain Dipteran species.

Specifically, the development of resistance in *Culex quinquefasciatus* to *Bacillus sphaericus* (B.s.) is noted by Rodcharoen et al., *Journal of Economic Entomology*, Vol. 87, No. 5, 1994, pp. 1133-1140. A method for overcoming this resistance, by combining B.s. with purified Cyt1A crystals isolated from *Bacillus thuringiensis* subsp. *israelensis* or by combining a recombinant B.t.i. with B.s., is disclosed by Wirth et al., *Journal of Medical Entomology*, Vol. 37, No. 3, 2000, pp. 401-407. However, improved but naturally derived or occurring biological larvicides and compositions to overcome *Culex* mosquito resistance to B.s. applications would be desirable. It is even more desirable if the biological Larvicide composition has the ability to effectively control broad spectrum mosquito species.

BRIEF SUMMARY OF THE INVENTION

The invention is directed to a novel method of combining a strain of *Bacillus thuringiensis* subspecies *israelensis* (ATCC Deposit Number SD-1276) and a strain of *Bacillus sphaericus* 2362 (ATCC Deposit Number, SD-1170) in which the individual strains are fermented in separate fermentation tanks, the activity of each strain is concentrated by a variety of methods including ultra filtration and centrifugation, and the slurry concentrates are combined in a suitable mix tank at pre-determined ratios to produce a combination slurry which may be spray dried to yield spray dried technical concentrate individual particles with toxins from both *Bacillus thuringiensis* subspecies *israelensis* and *Bacillus sphaericus*. This uniquely produced spray dried technical concentrate is further utilized to formulate wettable powders, granules, dry flowables or wettable granules or water dispersible granules, pellets, non-aqueous suspensions, briquettes, water soluble pouches and tablets which may be applied to mosquito habitats for enhanced and broad spectrum control of various mosquito species and also toward management of resistance that may inherently develop due to over use of biological larvicides such as *Bacillus sphaericus*. The strain of *Bacillus thuringiensis* subspecies *israelensis* may be genetically modified or non-genetically modified. The strain of *Bacillus sphaericus* may be genetically modified or non-genetically modified. The presently preferred combination includes a non-genetically modified strain of *Bacillus thuringiensis* subspecies *israelensis* and a non-genetically modified strain of *Bacillus sphaericus*.

The combination slurry may have from about 1:10 to about 10:1 weight ratio and or potency ratio of *Bacillus thuringiensis* subspecies *israelensis* to *Bacillus sphaericus*; preferably from about 1:4 to about 4:1 weight ratio of *Bacillus thuringiensis* subspecies *israelensis* to *Bacillus sphaericus*; more preferably from about 1:2 to about 4:1 weight ratio of *Bacillus thuringiensis* subspecies *israelensis* to *Bacillus sphaericus*; and most preferably a 4:1 potency ratio of *Bacillus thuringiensis* subspecies *israelensis* to *Bacillus sphaericus*.

Additional components such as surface active agents, inert carriers that may be natural, synthetic, organic or inorganic, natural and synthetic preservatives, humectants, feeding stimulants, attractants, encapsulating agents, binders, emulsifiers, dyes, sugars, sugar alcohols, starches, modified starches, dispersants, other polymers, vegetable and petroleum base oils, U.V. protectants, buffers, drift control agents, spray deposition aids, other stabilizers, free-flow agents or combinations thereof may also be utilized in conjunction with the combination in a larvicidal composition. The product form that may be used for delivery to mosquito habitats may be a technical powder, wettable powder, dust, pellet, briquette, tablet, impregnated granule (sand, corn cob, clay, synthetic), dry flowable or wettable granule or water dispersible granule or as non-aqueous or aqueous suspension concentrate. The biopotencies of thus combined product forms may range from 100 ITU/mg to 8000 ITU/mg for *Bacillus thuringiensis* subspecies *israelensis* and 25 Bs.ITU/mg to 3000 Bs.ITU/mg for *Bacillus sphaericus*. More preferably, biopotencies may range from 2000 ITU/mg to 6000 ITU/mg for *Bacillus thuringiensis* subspecies *israelensis* and 500 Bs.ITU/mg to 1500 Bs.ITU/mg for *Bacillus sphaericus* and most preferably the biopotencies may range from 1000 ITU/mg to 4000 ITU/mg for *Bacillus thuringiensis* subspecies *israelensis* and 250 Bs.ITU/mg to 1000 Bs.ITU/mg for *Bacillus sphaericus*.

The invention is also directed to a composition and a method of controlling Dipteran larvae comprising the step of introducing a larvicidally-effective amount of a composition containing a strain of *Bacillus thuringiensis* subspecies *israelensis* and a strain of *Bacillus sphaericus* prepared by the process of the present invention into an environment containing Dipteran larvae. In this method, Dipteran may be a mosquito such as *Culex pipiens, Culex quinquefasciatus, Aedes aegypti, Culex tarsalis, Culiseta incidens, Anopheles freeborni* or a combination thereof.

The invention is additionally directed to a method for inhibiting larvicidal resistance in Diptera comprising the step of introducing a larvicidally-effective amount of a composition containing a strain of *Bacillus thuringiensis* subspecies *israelensis* and a strain of *Bacillus sphaericus* that is prepared by the process of the present invention into an environment containing Dipteran larvae. Preferably, the Diptera is *Culex* and larvicidal resistance is developed against *Bacillus sphaericus*.

DETAILED DESCRIPTION OF THE INVENTION

The invention is directed to a method for controlling Dipteran larvae or a method for inhibiting larvicidal resistance in Diptera by introducing a larvicidally-effective amount of a novel combination of a strain of *Bacillus thuringiensis* subspecies *israelensis* and a strain of *Bacillus sphaericus* into an environment containing Dipteran larvae; and a composition of the combination. Preferably both strains are non-genetically modified. A detailed discussion of the composition, and the methods utilizing the composition follows.

The Larvicidal Compositions

Biopesticides are a class of naturally occurring pesticides frequently derived from unicellular or multicellular organisms which have developed natural defenses against other organisms. The group of microorganisms pathogenic to insects is varied and diverse. The gram-positive soil bacterium *Bacillus thuringiensis* subsp. *israelensis* is one of many *B. thuringiensis* strains able to produce insecticidal proteins. These proteins, expressed during the sporulation cycle of the bacterium, assemble into parasporal crystalline inclusion bodies. The parasporal crystal produced by *B. thuringiensis* subspecies *israelensis* is toxic when ingested by the larvae of Diptera, including mosquitoes and black flies. Upon ingestion, crystal proteins are solubilized in the larval midgut and disrupt the epithelium of the larval midgut region. Swelling and/or lysis of the epithelial cells is followed by larval death from starvation.

*Bacillus thuringiensis* subspecies *israelensis* (B.t.i.) has been used successfully in mosquito and blackfly control programs for many years. B.t.i. is utilized in clean to moderately clean organic breeding habitats, and is most effective on *Aedes* species. Commercial formulations of B.t.i. available under the trademark VECTOBAC® are available from Valent BioSciences Corporation. Specific commercial formulations available from the same supplier are VECTOBAC® G (5/8 Mesh corncob based granular formulation with a label claim of 200 ITU/mg), VECTOBAC® CG (1014 Mesh corncob based granular formulation with a label claim of 200 ITU/mg), VECTOBAC® 12AS (Aqueous suspension formulation with a lebel claim of 1200 ITU/mg) and VECTOBAC® or DF (Water dispersible granule or dry flowable formulation with a lebel claim of 3000 ITU/mg). B.t.i. is effective against a broad range of mosquito species, offers low mammalian toxicity and is easy to apply. B.t.i. also has a very low susceptibility to the development of resistance, because its larvacidal activity is based on multiple toxins. The probability that individual mosquitoes within a treated population will not be susceptible to all toxins is extremely small.

*Bacillus sphaericus* (B.s.) is a rod-shaped, aerobic, spore-forming bacterium found commonly in soil and other substrates. To date, at least 16 strains have been found to show mosquitocidal properties of various degrees. Several strains such as 1593M, 2362 and 2297 exhibit high toxicity to mosquito larvae. *Bacillus sphaericus* strain 2362, (VECTOLEX®, available from Valent BioSciences Corp.) has been utilized in many countries successfully. Specific commercial formulations of B.s. available from the same source are VECTOLEX® WDG (Water dispersible granular formulation with a label claim of 650 Bs. ITU/mg) and VECTOLEX® CG 1014 Mesh corncob granular formulation with a label claim of 50 Bs. ITU/mg). Moreover, this strain was found to perform well in controlling mosquitoes breeding in various habitats, especially ones with polluted water.

*Bacillus sphaericus* is most effective on *Culex* species. The activity of B.s. is due to a binary toxin, and repeated use of this toxin in the same habitats has been reported to lead to development of resistance.

However, various levels of resistance to B.s. by mosquito larvae have been observed in *Culex pipiens* and *Culex quinquefasciatus*.

We have now found that a combination of B.t.i. and B.s. is an effective larvicidal formulation. Non-genetically modified components are utilized, which are desirable if the larvicide is to be utilized in an environment connected with production or harvesting of food sources such as crops, cattle or swine. Non-genetically modified B.t.i. or B.s. may be defined as strains which occur naturally, and are not strains resulting from recombinant DNA techniques.

A novel method of combining B.t.i and B.s is illustrated in Example 1 which follows. The ratio of B.t.i. to B.s. may be from about 10:1 to about 1:10; preferably from about 4:1 to about 1:4, more preferably from about 4:1 to about 1:2 and most preferably about 4:1 B.t.i:B.s either on a solids or ITU basis.

The compositions disclosed above may also include additional components such as a surface active agent, an inert carrier, a preservative, a humectant, a feeding stimulant, an attractant, a drift control agent, a spray deposition aid, an encapsulating agent, a binder, an emulsifier, a dye, a U.V. protectant, a buffer, a free-flow agent, or any other component which stabilizes the active ingredient, facilitates product handling and application for the particular target pests, Diptera.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphate such as sodium dodecyl sulphate, sodium octadecyl sulphate or sodium acetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates; salts of sulphonated phenol-formaldehyde condensates; or more complex sulphonates such as the amide sulphonates, e.g., the sulphonated condensation product of oleic acid and N-methyltaurine or the dialkyl sulphosuccinates, e.g., the sodium sulphonate or dioctyl succinate.

Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxythylene sorbitan fatty acids esters, block copolymers of ethylene oxide and propylene oxide, acetylenic glycols such as 2,4,7,9-tetraethyl-5-decyn-4,7 diol, or ethoxylated acetylenic glycols.

Examples of a cationic surface-active agent include, for instance, an aliphatic mono-, di-, or polyamide as an acetate, naphthenate or oleate; an oxygen-containing amine such as an amine oxide of polyoxethylene alkylamine; an amid-linked amine prepared by the condensation of a carboxylic acid with a di- or polyamine; or a quaternary ammonium salt.

Examples of inert materials include inorganic minerals such as kaolin, mica, gypsum, fertilizer, sand, phyllosilicates, carbonates, sulphate, or phosphates; organic materials such as sugars, starches, or cyclodextrins; or botanical materials such as wood products, cork, powdered corncobs, rice hulls, peanut hulls, and walnut shells.

The formulation may also contain added drift control agents or spray deposition aids to control droplet size and to facilitate aerial application. Examples of suitable compounds for these purposes include polyvinylalcohol polymer solutions, polyamide copolymer solutions, polymerized acrylic acid derivatives and blends thereof, vegetable oils and blends thereof, petroleum oils and blends thereof, as well as natural and synthetic polymers.

In the formulations, more than one of the additional components described above may advantageously be utilized.

The compositions of the present invention can be applied as a liquid, an aqueous suspension, an emulsifiable suspension, or a solid by conventional application techniques for each. Solid formulations are presently preferred. In general, the application rate of the larvicidally-effective combination of the present invention will deliver a quantity of pesticide sufficient to control the population of a target pest.

Solid compositions may be formed by spray drying the B.t.i. and B.s slurries separately and combining the powder or by combining the slurries and spray drying the combined slurry to form a powder.

The composition of the present invention can be in a suitable product form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition may contain from about 1 to 98% by weight of a solid or liquid inert carrier, and 0.1 to 50% by weight of other suitable components such as a surfactant, a dispersant, a suspending agent, a free-flow agent, a stabilizing agent, UV protecting agent, a polymer or combination thereof. These compositions will be administered at the rate of about 50 g (liquid or dry) to 20 kg or more per hectare.

The Methods

The combination of the present invention can be treated prior to formulation to prolong the insecticidal activity when applied to the environment of a target pest as long as the pretreatment is not deleterious to the combination. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixatives.

The compositions of the invention can be applied directly to the environment to be treated. Ponds, lakes, streams, rivers, still water, and other areas subject to infestation by Dipteran pests are examples of environments needing such treatment. The composition can be applied by spraying, dusting, sprinkling, and broadcasting, among others.

The compositions of the present invention may be effective against insect pests of the order Diptera, e.g., *Aedes* sp., *Andes vittatus, Anastrepha ludens, Anastrepha suspensa, Anopheles* sp., *Armigeres subalbatus, Calliphora stygian, Calliphora vicina, Ceratitis capitata, Chironomus tentans, Chrysomya rufifacies, Cochliomyia macellaria, Culex* sp., *Culiseta* sp., *Coquillettidia* sp., *Deino cerities* sp., *Dacus oleae, Delia antiqua, Delia platura, Delia radicum, Drosophila melanogaster, Eupeodes corollas, Glossina austeni, Glossina brevipalpis, Glossina fuscipes, Glossina moristans centralis, Glossina morsitans morsitans, Glossina morsitans submorsitans, Glossina pallidipes, Glossina palpalis gambiensis, Glossina palpalis palpalis, Glossina tachinoides, Haemagogus equines, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mansonia* sp., *Mayetiola destructor, Musca autumnalis, Musca domestica, Neobellieria* sp., *Nephrotoma suturalis, Ochlerotatus* sp., *Ophyra aenescens, Orthopodomyia* sp., *Phaenicia sericata, Phlebotomus* sp., *Phormia regina, Psorophora* sp., *Sabethes cyaneus, Sarcophaga bullata, Scatophaga stercoraria, Stomoxys calcitrans, Toxorhynchites amboinensis, Tripteroides bambusa, Uranotaneia* sp. and *Wyeomyia* sp. However, the composition of the invention may also be effective against insect pests of the order *Lepidoptera*, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylis hospes, Collas eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola,*

*Eupoecilia ambiguella, Euproctis chrysorrhoea, Euxoa messoria, Galleria mellonella, Grapholita molesta, Harrisinia americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma sp., Mamestra brassicae, Mamestra configurata, Manduca quinquemaculata, Manduca sexta, Maruca testulalis, Melanchra picta, Operophtera brumata, Orgyia sp., Ostrinia nubilalis, Paleacritia vemata, Papilla cresphontes, Pectinophora gossypiella, Phryganidia californica, Phyllonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera sp., Thaurnstopoea pityocampa, Tineloa bisselliella, Trichoplusia ni, Udea rubigalis, Xylomyges curialis, Yponomeuta padella*; Coleoptera, e.g., *Leptinotarsa sp., Acanthoscelides obtectus, Callosobruchus chinensis, Epilachna varivestis, Pyrrhalta luteola, Cylas formicarius elegantulus, Listronotus oregonensis, Sitophilus sp., Cyclocephala borealis, Cyclocephala immaculata, Macrodactylus subspinosus, Popillia japonica, Rhizotrogus majalis, Alphitobius diaperinus, Palorus ratzeburgi, Tenebrio molitor, Tenebrio obscurus, Tribolium castaneum, Tribolium confusum, Tribolius destructor*, Acari, e.g., *Oligonychus pratensis, Panonychus ulmi, Testranychus urticae*; Hymenoptera, e.g., *Iridomyrmex humilis, Solenopsis invicta*; Isoptera, e.g., *Reticulitermes hesperus, Reticulitermes flavipes, Coptotermes formosanus, Zootermopsis angusticollis, Neotermes connexus, Incisitermes minor, Incisitermes immigrans*; Siphonaptera, e.g., *Ceratophyllus gaffinae, niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans*; and Tylenchida, e.g., *Melodidogyne incognita, Pratylenchus penetrans.*

In a specific embodiment, the compositions of the invention are active against insect pests of the sub order Nematocera of the order Diptera. Nematocera include the families Culicidae, Simulidae, Chironomidae, Psychodidae, Sciaridae, Phoridae and Mycetophilidae.

The ability of combination of the present invention to inhibit larvicidal resistance is described in detail hereinafter in the Examples. These Examples are presented to describe preferred embodiments and utilities of the invention and are not meant to limit the invention unless otherwise stated in the claims appended hereto.

EXAMPLE 1

The most preferred and novel method of combining two biological actives is by pre-mixing fermentation beers or slurry concentrates of B.t.i and B.s at the desired solids or potency level and spray drying the slurry mixture to produce a combined technical spray dried powder concentrate. In such a combination formulation, the slurry concentrates may contain preservatives, stabilizers, surfactants, dispersants and other binders. The spray-dried technical concentrate or powder may then be utilized in formulating a granular product as wettable powders, water dispersible granules, and aqueous or non-aqueous suspension concentrates. These powder concentrates may also be utilized in pellet, tablet, and briquette formulations. A spray drying experiment was performed combining Bti and Bs fermentation slurry concentrates at various ratios based on % solids level in each of the slurry concentrates. A B.t.i slurry concentrate was first preserved with 0.12% wt/wt of potassium sorbate and 0.06% wt/wt of methyl paraben. Percent solids in the preserved B.t.i slurry concentrate were 11.3% wt/wt. Similarly, a B.s slurry concentrate was preserved with 0.12% wt/wt of potassium sorbate and 0.06% wt/wt of methyl paraben. Percent solids in the preserved B.s slurry concentrate had a mean % solids of 10.1% wt/wt. Slurry mixtures prepared and their ratios on solids basis are given in Table 1.

TABLE 1

B.t.i and B.s slurry mixtures evaluated

| | Material\Ratio of B.t.i to B.s on solids basis | | | | | |
|---|---|---|---|---|---|---|
| | 1:0 A | 1:1 B | 3:1 C | 1:3 D | 2:1 E | 1:2 F |
| B.t.i preserved slurry concentrate | 8.85 Kg | 4.42 Kg | 6.64 Kg | 2.21 Kg | 5.89 Kg | 2.95 Kg |
| B.s preserved slurry concentrate | — | 5.10 Kg | 2.55 Kg | 7.65 Kg | 3.41 Kg | 6.80 Kg |
| De-ionized water | 1.15 Kg | 0.48 Kg | 0.81 Kg | 0.14 Kg | 0.70 Kg | 0.25 Kg |
| Total | 10.0 Kg | 10.0 Kg | 10.0 Kg | 10.0 Kg | 10.0 Kg | 10.0 Kg |

The compositions as shown in Table 1 were combined and spray dried utilizing a Niro spray dryer. Inlet temperature ranged between 180° C. and 190° C. and outlet temperature during drying ranged between 68° C. to 81° C. The technical powders were sieved through 100-mesh standard sieve and samples were bioassayed against L4 *Aedes aegypti* and L3 *Culex quinquefasciatus*. Average potency data is represented in Table 2.

TABLE 2

Potency values of B.t.i + B.s. spray dried technical powders as affected by their ratios on solids basis. Mean B.t.i spray dried technical powder potency = 7474 ITU/mg. Mean B.s spray dried technical powder potency = 3030 Bs. ITU/mg (All assays are average of initial and 2 month 5° C. stored samples)

| Ratio of B.t.i to B.s on solids basis | Theoretical B.t.i Potency* (ITU/mg) | Actual B.t.i Potency (ITU/mg) | Actual Potency expressed as % of theoretical potency in Column 2. | Theoretical B.s Potency + (Bs. ITU/mg) | Actual B.s Potency (Bs. ITU/mg) | Actual Potency expressed as % of theoretical potency in Column 5 |
|---|---|---|---|---|---|---|
| 1:1 | 3737 | 5174 | 138% | 1515 | 1642 | 108% |
| 3:1 | 5606 | 6122 | 109% | 758 | 1088 | 144% |
| 1:3 | 1869 | 4769 | 255% | 2273 | 2655 | 117% |
| 2:1 | 4983 | 5499 | 110% | 1009 | 1479 | 147% |
| 1:2 | 2489 | 3738 | 150% | 2020 | 2503 | 124% |
| Mean | 3737 | 5060 | | 1515 | 1873 | |

Biopotency data presented in Table 2 reveal an interesting but very synergistic increase in actual potency of both B.t.i and B.s over theoretical potencies, which are, based on actual potencies of 100% of either B.t.i or B.s spray dried technical powders. The best combination for increased activity on both *Aedes* and *Culex* appeared to be when B.t.i and B.s slurry concentrates are combined at 1 part of B.t.i to 2 parts of B.s on solids basis. For enhancing the B.s potency, the best combination was when two parts of B.t.i solids was combined with 1 part of B.s solids. In this combination, B.s potency showed 47% increase over theoretical potency. By combining the B.t.i and B.s slurry concentrates prior to spray drying, B.t.i potency on average showed an increase of 35% over mean theoretical mean potency while B.s potency showed an increase of 24% over theoretical mean potency. There appeared to be significant advantage in combining the slurry concentrates prior to spray drying and further formulating these powders as granules, wettable powders, water dispersible granules, or pellet formulations. The best possible explanation for these enhanced potency values appeared to be due to the fact that each spray dried particle carries both B.t.i and B.s toxins and spores. Thus, these novel formulation approaches are likely to not only result in broad-spectrum activity but also will minimize the potential for build up of resistance. In other words, resistance management can also be achieved yet by another novel formulation approach.

EXAMPLE 2

Example of Changes in Susceptibility of *Bacillus Sphaericus* Susceptible *Culex Pipiens Quinquefasciatus* Colonies Upon Selection with *Bacillus Sphaericus* and Two B.t.i: B.s. Technical Dry Formulations Derived by Combining both Fermentation Slurry Formulations and Spray Drying This experiment was conducted using *Culex pipiens quinquefasciatus* colonies established from susceptible field populations collected in Thailand. The field mosquitoes were collected from an area known to have a high potential for development of resistance to *Bacillus sphaericus*. The colonies were subjected to selection each generation at the $LC_{80}$ level with the following materials.

1. Untreated Control—(no selection)
2. B.s technical powder
3. 1:1 ITU ratio B.t.i: B.s Technical Spray Dried Formulation (VBC-60033)
4. 4:1 ITU ratio B.t.i: B.s Technical Spray Dried Formulation (VBC-60034)

The colonies were assayed for susceptibility to *Bacillus sphaericus* prior to the selections and each fifth generation for twenty-five generations. The colonies were bioassayed by placing 20 late third or early fourth instar larvae in a 116 ml waxed paper cup containing 100 ml distilled water. One drop of larval diet (2 g of ground up rabbit pellets in 20 ml distilled water) was added per cup. The cups were treated with a range of concentrations of each formulation. Five to seven different concentrations were utilized in each bioassay to yield mortalities. Each concentration was replicated four to five times in each test. The treated larvae were held at 82-85° F. To determine $LC_{50}$ values, the number of dead larvae was counted at regular intervals from the time of treatment with the test larvicide. Once all larvae died, the concentration wherein 50% had been killed could be determined.

The following table shows the changes in $LC_{90}$ values in each of the selected colonies over 25 generations. Susceptibility of B.s selected colonies decreased, while colonies selected with VBC-60033 and VBC-60034 (Formulations derived by combining fermentation slurry concentrates and spray drying) maintained stable susceptibilities relative to the unselected colony.

TABLE 3

$LC_{90}$ VALUES OF EACH FIFTH GENERATION AFTER SELECTION

| TREATMENTS | F-0 $LC_{90}$ ppm | F-5 $LC_{90}$ ppm | F-10 $LC_{90}$ ppm | F-15 $LC_{90}$ ppm | F-20 $LC_{90}$ ppm | F-25 $LC_{90}$ ppm |
|---|---|---|---|---|---|---|
| Unselected | 0.013 | 0.022 | 0.03 | 0.022 | 0.061 | 0.034 |
| B.s @ LC80 | 0.013 | 0.075 | 0.149 | 2.332 | 1.256 | 1.551 |
| VBC-60033 @ LC80 | 0.013 | 0.074 | 0.022 | 0.049 | 0.048 | 0.047 |
| VBC-60034 @ LC80 | 0.013 | 0.007 | 0.024 | 0.03 | 0.021 | 0.022 |

EXAMPLE 3

Example of Changes in Susceptibility of *Bacillus Sphaericus* Resistant *Culex Pipiens Quinquefasciatus* Colonies Upon Selection with Two B.t.i:B.s Technical Dry Formulations Derived by Combining Both B.t. and B.s Fermentation Slurry Formulations and Spray Drying A resistant colony is one that demonstrates a significant decrease in susceptibility to a particular pesticide over that expected for wild type insects. Generally, a five-fold or more decrease in susceptibility indicates resistance. Rodcharoen et al., *Journal of Economic Entomology*, Vol. 87, No. 5, 1994, pp. 1133-1140 explores the concept of resistance more fully.

A susceptible colony is one that is effectively killed by a particular pesticide. For example, in *Culex quinquefasciatus*, if a particular pesticide, *Bacillus sphaericus*, has a measured $LC_{50}$ value of less than 0.1 ppm, the colony is characterized as susceptible to that pesticide.

The change in susceptibility of *Culex quinquefasciatus* laboratory colonies known to be B.s. resistant, in response to selections with VBC-60033 and VBC-60034 (Technical dry formulations derived by combining fermentation slurry concentrates of both B.t.i and B.s and spray drying) were determined in the laboratory in the following manner. Selection refers to treatment at less than $LC_{100}$ level.

A colony of *Culex quinquefasciatus* resistant to B.s. was started from highly resistant larvae collected from a water body in Wat Pikul, Bang Yai District, Nonthaburi Province, Thailand. Field collected larvae were subjected to selection at $LC_{80}$ every generation for twenty generations. At the $20^{th}$ generation, the colony showed a 47,000 and 1,153,846 fold resistance at $LC_{50}$ and $LC_{90}$ levels respectively. This colony was used for subsequent tests.

The experiment was conducted using sub-colonies established from the highly B.s. resistant colonies. The colonies were subjected to selection each generation at the $LC_{80}$ level with the following materials.

1. 1:1 ITU ratio B.t.i:B.s or VBC-60033 (Technical dry formulation derived by combining B.t.i and B.s fermentation slurry formulations and spray drying)
2. 4:1 ITU ratio B.t.i:B.s or VBC60034 (Technical dry formulation derived by combining B.t.i and Bsph fermentation slurry formulations and spray drying)

The colonies were assayed for susceptibility to B.s prior to the selections and at each fifth generation for twenty-five generations of selection. Bioassay methods described in Example 2 were also used in this experiment.

The following table shows the changes in $LC_{90}$ values in each of the selected colonies over 25 generations. $LC_{90}$ of the 4:1 B.t.i:B.s or VBC-60034 (Technical dry formulation derived by combining B.t.i and B.s fermentation slurry formulations and spray drying) selected colony was 157 times lower than the unselected colony after 25 generations of selection.

TABLE 4

$LC_{90}$ VALUES OF EACH FIFTH GENERATION FOLLOWING SELECTIONS

| TREATMENTS | F-0 $LC_{90}$ ppm | F-5 $LC_{90}$ ppm | F-10 $LC_{90}$ ppm | F-15 $LC_{90}$ ppm | F-20 $LC_{90}$ ppm | F-25 $LC_{90}$ ppm |
|---|---|---|---|---|---|---|
| Unselected | 267231 | 56565 | 19851 | 20451 | 17021 | 19331 |
| VBC-60033 @ LC80 | 15000 | 20860 | 10989 | 1334 | 1304 | 353 |
| VBC-60034 @ LC80 | 15000 | 29642 | 531 | 206 | 107 | 123 |

EXAMPLE 4

Example of Effectiveness of B.t.i:B.s. (VBC-60033 and VBC-60034) for Control of B.s Susceptible Mosquito Larvae Tests were carried out in controlled small plots infested with mosquito larvae. Plastic wading pools infested with larvae via natural oviposition were used. Species present included *Culex pipiens* and *Culiseta incidens*. Plots were filled with water, then enriched with ~100 g of rabbit chow each. Yard waste was added to provide substrate, and the plots were left to infest for two weeks. Plots were infested with roughly equivalent numbers of L1-L3 larvae at the initiation of the test.

The following treatments were made:

1) UTC

2) VectoBac® CG (200 ITU B.t.i)

3) VectoLex® CG (50 Bs. ITU)

4) VBC-60035 (4:1 ITU B.t.i:B.s granules using VBC-60034)

5) VBC-60037 (1:1 ITU B.t.i.B.s granules using VBC-60033)

Rates: All materials were applied at 2.55 kg/ha (200 gm/plot)

Test Design:

Replication—5 replicates

Randomization—Modified RCB based on initial populations.

Total plots used=25

Plot size=0.785 sq meters

Sampling: All plots were sampled by dipping prior to treating the plots. Post treatment samples were taken on days 3, 7, 14, 21 and 28 following treatment. Four dips were taken per plot. Time was allowed between dips for larvae to re-surface in each plot. This was accomplished by taking the first dip from all the plots, then returning to the first plot for the second dip, taking the second dip from all plots and continuing in a like fashion for all four dips. Total number of L1-L2, L3-L4 and pupae collected in each plot were counted and recorded.

Results

Populations of L3-L4 larvae were initially reduced by all treatments. Reductions achieved by ABG-6185, VBC-60035 and VBC-60037 were similar throughout the study, and were significantly lower than the UTC on days 3 to 21 ($p=0.05$). Reductions achieved by ABG-6138S were statistically lower than UTC on days 3-14, but higher than the other three treatments on days 7 to 28 ($p=0.05$). L3-L4 Population trends are shown in the following table. Both VBC-60035 and VBC-60037 formulations provided high levels of initial and residual control.

TABLE 5

POPULATION TRENDS IN PLOTS LARGE LARVAE/4 DIPS

| | DAY 0 | DAY 3 | DAY 7 | DAY 14 | DAY 21 | DAY 28 |
|---|---|---|---|---|---|---|
| UTC | 312 | 735 | 345 | 376 | 326 | 278 |
| ABG-6138S | 293 | 43 | 76 | 118 | 182 | 249 |
| ABG-6185 | 317 | 6 | 1 | 1 | 27 | 103 |
| VBC-60035 | 262 | 1 | 0 | 7 | 52 | 93 |
| VBC-60037 | 254 | 10 | 1 | 28 | 11 | 56 |

EXAMPLE 5

Example of Effectiveness of B.t.i: B.s Formulations for Control of *Bacillus Sphaericus* Tolerant Mosquito Larvae Efficacy studies of Vectobac® CG (B.t.i @200 ITU/mg) and VBC-60035 at an application rate of 1.25 lb/acre were conducted in small field plots against colony reared Ochlerotatus taeniorhynchus $2^{nd}/3^{rd}$ instar larvae. This mosquito species is tolerant to B.s exposure. The formulations were added to the plots following flooding and larval introduction.

Approximately 1000 $2^{nd}/3^{rd}$ instar *Oc. taeniorhynchus* larvae were reared in the laboratory and added to each plot at the time of flooding. The water surface area in the plots measured approximately 8 $ft^2$ with a depth of approximately 6" and a salinity of 3-5 ppt (Floore et al. 1998). Emergent grasses were present in all the plots. The water temperature (not yet available) was recorded using an Onset HOBO ProSeries Temperature data recorder and the salinity measured with a Salinity Refractometer (SR-1). The pH was recorded with Oakton pH Tester 2 (not yet available). The study was initiated Jun. 19, 2003. Rainfall during the study was 3.5".

The randomized study consisted of 4 replications of the treatments of the formulations and untreated control plots. The application rates were based on the plot surface area and weighed on a Mettler electronic balance and applied by hand. Larvae were fed daily approximately 100 ml of larval food (3 parts liver powder:2 parts brewer's yeast).

The following treatments were made:

1) UTC

2) VectoBac® (B.t.i. @ 200 ITU/mg)

3) VBC-60035 (4:1 of B.t.i:B.s with 200 ITU/mg+50 Bs.ITU/mg on Corncob granules)

Rates: Materials were applied at 1.25 lb/a

Sampling: All plots were sampled by dipping the plots. Post treatment samples were taken at 24 and 48 hours following treatment. Eight dips were taken per plot. Numbers of larvae collected by dipping were counted and recorded.

Results

Mean larval numbers sampled in plots treated with VBC-60035 formulation were lower than in the plots treated with B.t.i and significantly lower than in the UTC at both 24 and 48 hours following treatment. Corrected percent reductions in the plots treated with the VBC-60035 were 71% and 92% at 24 and 48 hours respectively. Like values in the B.t.i treated plot were 65% and 81%.

TABLE 6

MEAN NUMBER OF LARVAE SAMPLED
IN PLOTS AT 24 AND 48 HOURS AFTER TREATMENTS

| TREATMENT | 24 HRS | 48 HRS |
|---|---|---|
| UTC | 12.75 c | 41.25 c |
| VectoBac ® CG | 4.5 ab | 8 ab |
| VBC-60035 | 3.75 a | 3.25 a |

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

The invention claimed is:

1. A method of controlling Dipteran larvae comprising the step of:
introducing a larvicidally-effective amount of a combination of a strain of *Bacillus thuringiensis* subspecies *israelensis* and a strain of *Bacillus sphaericus* into an environment containing Dipteran larvae, wherein said combination has from about 1:3 to about 3:1 weight ratio of *Bacillus thuringiensis* subspecies *israelensis* to *Bacillus sphaericus*.

2. The method of claim 1, wherein said strain of *Bacillus thuringiensis* subspecies *israelensis* is non-genetically modified.

3. The method of claim 1, wherein said strain of *Bacillus sphaericus* is non-genetically modified.

4. The method of claim 1, wherein said strain of *Bacillus thuringiensis* subspecies *israelensis* is non-genetically modified and said strain of *Bacillus sphaericus* is non-genetically modified.

5. The method of claim 1, wherein said combination has from about 1:2 to about 2:1 weight ratio of *Bacillus thuringiensis* subspecies *israelensis* to *Bacillus sphaericus*.

6. The method of claim 1, wherein said combination has a 1:1 ratio of *Bacillus thuringiensis* subspecies *israelensis* to *Bacillus sphaericus*.

7. The method of claim 1, wherein said Dipteran is a mosquito.

8. A method for inhibiting larvicidal resistance in Diptera comprising:
the step of introducing a larvicidally-effective amount of a combination of a strain of *Bacillus thuringiensis* subspecies *israelensis* and a strain of *Bacillus sphaericus* into an environment containing Dipteran larvae, wherein said combination has from about 1:3 to about 3:1 weight ratio of *Bacillus thuringiensis* subspecies *israelensis* to *Bacillus sphaericus*.

9. The method of claim 8, wherein said strain of *Bacillus thuringiensis* subspecies *israelensis* is non-genetically modified.

10. The method of claim 8, wherein said strain of *Bacillus sphaericus* is non-genetically modified.

11. The method of claim 8, wherein said strain of *Bacillus thuringiensis* subspecies *israelensis* is non-genetically modified and said strain of *Bacillus sphaericus* is non-genetically modified.

12. The method of claim 8, wherein said combination has from about 1:2 to about 2:1 weight ratio of *Bacillus thuringiensis* subspecies *israelensis* to *Bacillus sphaericus*.

13. The method of claim 8, wherein said combination has a 1:1 ratio of *Bacillus thuringiensis* subspecies *israelensis* to *Bacillus sphaericus*.

14. The method of claim 8, wherein said Diptera is *Culex*.

15. The method of claim 8, wherein larvicidal resistance is developed against *Bacillus sphaericus*.

16. The method of claim 8, wherein said Diptera is a mosquito.

17. The method of claim 7, wherein said mosquito is selected from the group consisting of *Culex pipiens*, *Culex quinquefasciatus*, *Aedes aegypti*, *Culex tarsalis*, *Culiseta incidens*, *Anopheles freeborni* and combinations thereof.

18. The method of claim 16, wherein said mosquito is selected from the group consisting of *Culex pipiens*, *Culex quinquefasciatus*, *Aedes aegypti*, *Culex tarsalis*, *Culiseta incidens*, *Anopheles freeborni* and combinations thereof.

19. A composition comprising:
a combination of a strain of *Bacillus thuringiensis* subspecies *israelensis* and a strain of *Bacillus sphaericus*, wherein said combination has from about 1:3 to about 3:1 weight ratio of *Bacillus thuringiensis* subspecies *israelensis* to *Bacillus sphaericus*.

20. The composition of claim 19, wherein said strain of *Bacillus thuringiensis* subspecies *israelensis* is non-genetically modified.

21. The composition of claim 19, wherein said strain of *Bacillus sphaericus* is non-genetically modified.

22. The composition of claim 19, wherein said strain of *Bacillus thuringiensis* subspecies *israelensis* is non-genetically modified and said strain of *Bacillus sphaericus* is non-genetically modified.

23. The composition of claim 19, wherein said combination has from about 1:2 to about 2:1 weight ratio of *Bacillus thuringiensis* subspecies *israelensis* to *Bacillus sphaericus*.

24. The composition of claim 19, wherein said combination has a 1:1 ratio of *Bacillus thuringiensis* subspecies *israelensis* to *Bacillus sphaericus*.

25. The composition of claim 19 further comprising an additional component selected from the group consisting of a surface active agent, an inert carrier, a preservative, a humectant, a feeding stimulant, an attractant, an encapsulating agent, a binder, an emulsifier, a dye, a ultra violet light protectant, a buffer, a drift control agent, a spray deposition aid, a free-flow agent and combinations thereof.

26. The composition of claim 19, wherein slurries of both strains are spray dried.

27. The composition of claim 26, wherein the slurries are spray dried separately.

28. The composition of claim 26, wherein the slurries are mixed together and the mixture is spray dried.

* * * * *